United States Patent
Turner et al.

(10) Patent No.: US 6,329,531 B1
(45) Date of Patent: Dec. 11, 2001

(54) OPTICAL DIAGNOSTIC AGENTS FOR DIAGNOSIS OF NEURODEGENERATIVE DISEASES BY MEANS OF NEAR INFRARED RADIATION (NIR RADIATION)

(75) Inventors: Jonathan Turner, Berlin; Thomas Dyrks, Hohenneuendorf; Wolfhard Semmler, Berlin; Kai Licha, Berlin; Bjorn Riefke, Berlin, all of (DE)

(73) Assignee: Schering AG, Berkin (DE)

( * ) Notice: Subject to any disclaimer, the term of this patent is extended or adjusted under 35 U.S.C. 154(b) by 0 days.

(21) Appl. No.: 09/308,177

(22) PCT Filed: Oct. 29, 1997

(86) PCT No.: PCT/DE97/02559

§ 371 Date: Nov. 18, 1999

§ 102(e) Date: Nov. 18, 1999

(87) PCT Pub. No.: WO98/22146

PCT Pub. Date: May 28, 1998

(30) Foreign Application Priority Data

Nov. 19, 1996 (DE) .............................. 196 49 971

(51) Int. Cl.$^7$ ....................... G01N 33/51; G01N 35/533; A61K 49/00; C09B 57/04; C09B 56/16
(52) U.S. Cl. ........................ 548/455; 424/9.34; 424/9.6; 534/747; 534/822; 536/26.6; 536/29.11; 536/29.13; 548/362.5; 548/364.7
(58) Field of Search .............................. 548/362.5, 462, 548/455, 364.7; 534/747, 822; 424/9.34, 9.6; 536/26.6, 29.11, 29.13

(56) References Cited

FOREIGN PATENT DOCUMENTS

| 4-194841 | 7/1992 | (JP) . |
| 9617628 | 6/1996 | (WO) . |

OTHER PUBLICATIONS

Graebert KS et al (Laboratory Investigations), vol. 72, No. 5, pp. 513 to 523, May 1995.*
Pareser DM et al (Neuron), vol. 17, No. 3, pp. 553 to 565, Sep. 1996.*
Reiffers S et al (INT. J. Appl. Rapiat. Isot.), vol. 34, No. 9, pp. 1383–1393, 1983.*
Paresce DM et al: "Microglial cells internalize aggregates of the Alzheimer's disease amyloid beta–protein via a scavenger receptor." Neuron Sep. 1996, vol. 17, No. 3, pp. 553–565.
Thanos S.: "Function–dependent labelling of microglial cells by means of carbocyanine dyes in vivo" Clin. Neuropathol., 1993, vol. 12, No. 5, pp. 298–301.
Murphy G M et al: "Development of a monoclonal antibody specific for the cooh–terminal of Beta–amyloid 1–42 and its immunohistochemical Reactivity in alzheimer's disease and related disorders" American Journal of Pathology, Bd. 144, Nr. 5, 1. Mai 1994, Seiten 1082–1088.

Heegaard N H H et al: "Demonstration of a heparin–binding site in serum amyloid P component using affinity capillary electrophoresis as an adjunct technique" Journal of Chromatography A, Bd. 1, Nr. 717, 24, Nov. 1995, Seite 83–90.

Malle E et al: "Quantification and mapping of antigenic determinants of serum amyloid A (SAA) protein utilizing sequence–specific immunoglobulins and Euas a specific probe for time–resolved fluorometric immunoassay" Journal of Immunological methods, Bd. 1, Nr. 182, 11. Mai 1995, Seite 131–144.

Reiffers et al: "Cyclotron isotopes and radiopharmaceuticals –XXXIII. Synthesis and structual effects of selective biliary excretion of halogenated indotricarbocyanines" Int. J. Appl. Radiat. Isot., 1983, vol 34, No. 9, pp. 1383–1393.

Mank A J G et al: "Visible Diode Laser–induced Fluorescence Detection in Liquid Chromatography After Precolumn Derivatization of Amines"Analytical Chemistry, BD. 67, 1995, Seiten 1742–1748.

Foley P et al: "Evidence for the Presence of Antibodies to Chrolinergic Neurons in the Serum of Patients with alzheimer's disease" Journal of Neurology –Zeitschrift Fuer Neurologie, Bd, 235, 1988, Seiten 466–471.

Ernst L A et al: "Cyanine Dye labeling Reagents for Sulfhydrul Groups" Cytometry, Bd, 10, Nr. 1, 1. Januar 1989, Seiten 3–10.

Shigeo Yasui et al: "Syntheses and some Properties of infrared–Absorbing Croconium and related Dyes" Dyes and Pigments, Bd. 10, Nr. 1, 1989, Seiten 13–22.

Narayanan N et al: "A New Method for the Synthesis of Heptamethine Cyanine Dyes: Synthesis of New near–infrared fluorescent labels" Journal of Organic Chemistry, Bd. 60, 1995, Seiten 2391–2395.

(List continued on next page.)

Primary Examiner—Floyd D. Higel
(74) Attorney, Agent, or Firm—Millen, White, Zelano & Branigan, P.C.

(57) ABSTRACT

The invention relates to compounds of formula (I): $F_m(-A1)(-B_n)(-W_o)$ wherein F is a colorant-signal molecule with a maximum absorption value ranging from 600–1200 nm; A is a β-amyloid plaque binding biomolecule; B is a β-amyloid plaque binding colorant; and W is a β-amyloid plaque binding hydrophilic low-molecular structural element. The invention also describes the use of these compounds in in vivo an din vitro diagnosis of neurodegenerative diseases such as Alzheimer's disease by means of near infra-red radiation (NIR radiation) as a constrasting agent in fluoresecence and transillumination diagnosis in the NIR range. Diagnostic agents containing said componenets are also disclosed.

21 Claims, 2 Drawing Sheets

OTHER PUBLICATIONS

Figure 1:
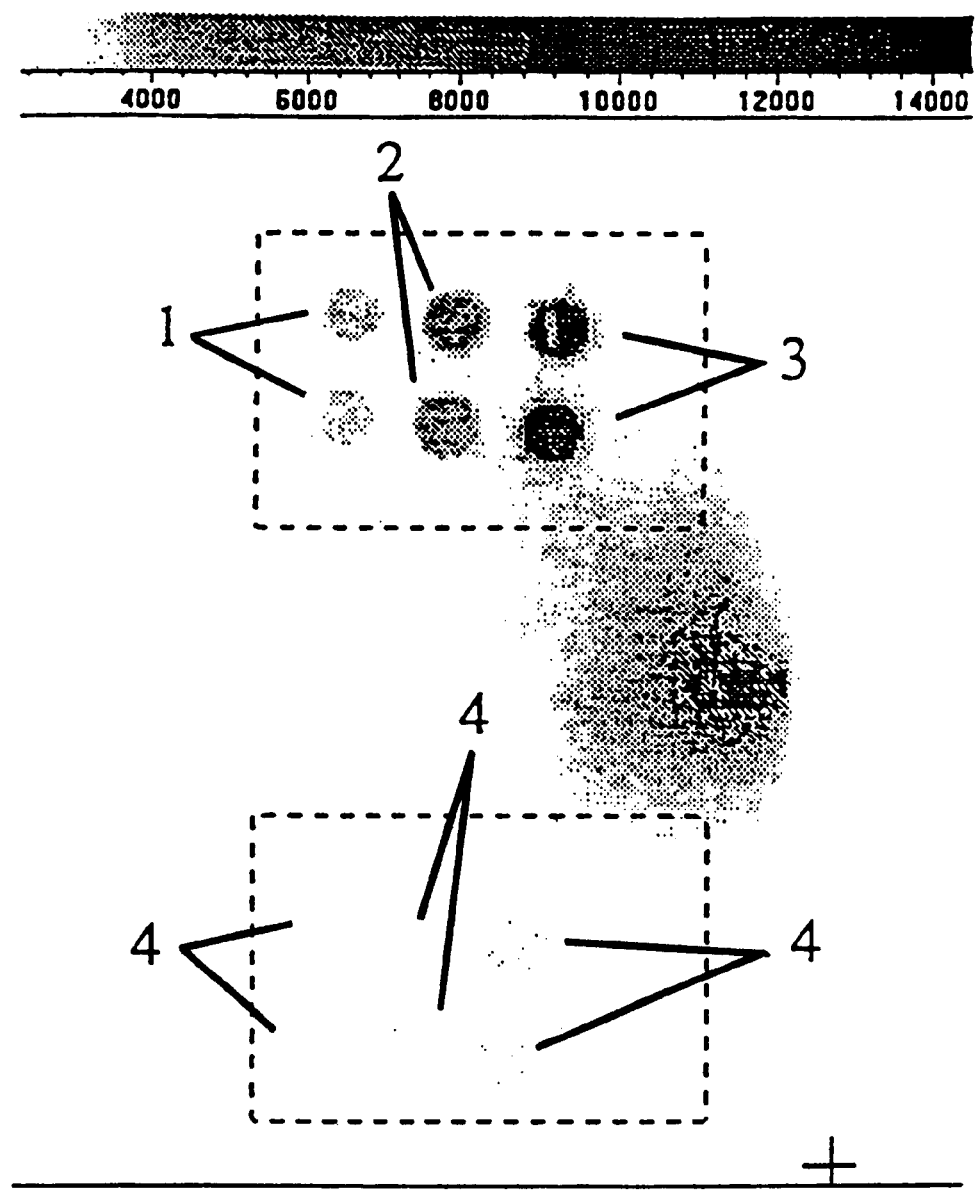

Database Dissab University Microfilms International An: AAD97–16685, Williams, Richard James, III: "Development of a Solid Phase Immunoassay for the Detection of Human Immunoglobulin G: A Novel Bio–Analytical Application of Semiconductor laser induced near–infrared Fluorescence"XP002073426 & Dissertation Abstracts International. vol. 57, No: 12, Section: B, p. 7499, Abstract of Ph.D. Thesis, 1996, Georgia University, 213 Pages.

Database Dissab University Microfilms International An: AAD97–16685, Williams, Richard James, III: "Development of a solid Phase Immunoassay for the Detection of Human Immunoglobulin G: A novel Bio–Analytical Application of Semiconductor Laser induced near–infrared fluorescence"XP002073426 & Dissertation abstracts International vol. 57, No. 12, Section: B, p. 7499. Abstract of Ph.D. Thesis, 1996, Georgia University, 213 pages.

Graebert KS et al: "Localization and regulated release of Alzheimer amyloid precursor–like protein in thyrocytes." Laboratory Investigations, May 1995, vol. 72, No. 5, pp.513–523.

Belloc F et al: "Selective Staining of Immature Hemopoietic cells with Merocyanine 540 in flow Cytometry" Cytometry, Bd. 9, Nr. 1, 1, Januar 1988, Seiten 19–24.

Williams R J et al: "Instrument to Detect near–infrared Fluorescence in solid–Phase Immunoassay" Analytical Chemistry, Bd. 66, Nr. 19, 1 Oktober 1994, Seiten 3102–3107.

Mujumdar R B et al: "Cyanine Dye Labeling Reagents: Sulfoindocyanine Succinimidyl Esters" Bioconjugate Chemistry, Bd. 4, Nr. 2, Maerz 1993, Seiten 105–111.

* cited by examiner

OPTICAL DIAGNOSTIC AGENTS FOR DIAGNOSIS OF NEURODEGENERATIVE DISEASES BY MEANS OF NEAR INFRARED RADIATION (NIR RADIATION)

The invention relates to compounds for in-vivo and in-vitro diagnosis of neurodegenerative diseases by means of near infrared radiation (NIR radiation), the use of these compounds as optical diagnostic agents and diagnostic agents that contain these compounds.

Alzheimer's disease (AD) is the most common form of advanced dementia in older humans. The frequency of occurrence of AD increases with the age of the patient and reaches values of 40%–50% in the age group between 85 and 90 years. AD can be diagnosed with certainty only post mortem by the study of the brain of the patient in an autopsy. The brains of Alzheimer patients contain many characteristic amyloid plaques in the neuronal tissue and in the surrounding area of blood vessels that are surrounded by dystrophied neurites and neurofibrillar "tangles." The brains of Alzheimer patients also show a small number of synapses. In the advanced stage of the disease, a far-reaching degeneration of neuronal structures and a significant decrease in brain volume has been determined (Wiesniewski, H. M., Weigel, J., Alzheimer's Disease Neuropathology. Current Status of Interpretation of Lesion Development. Ann NY Acad Sci 1992, 673: 270–84).

The amyloid plaques consist of, i.a., the amyloid-β-peptide (Aβ), a fragment of the β-amyloid precursor protein (APP) that consists of 40 to 42 amino acids (Master, C. L.; Simms, G.; Weinman, N. A., et al. Amyloid Plaque Core Protein in Alzheimer Disease and Down Syndrome. Proc Natl Acad Sci USA 1985, 82: 4245–9; Kang, J., Lemaire, H. G., Unterbeck, A. et al. The Precursor of Alzheimer's Disease Amyloid A4 Protein Resembles a Cell-Surface Receptor. Nature 1987, 325: 733–6). The number of plaques does not correlate to the degree of advanced dementia, but it is an early and reliable diagnostic agent for the occurrence of Alzheimer's disease. This results in the hypothesis that the first deposits of Aβ take place long before the manifestation of AD and before the first clinical symptoms occur (Hardy, L.; Allsop, D., Amyloid Deposition as the Central Event in the Aetiology of Alzheimer's Disease. Trends Pharmacol Sci 1991, 12: 383–8).

A method that provides for quantitative early detection of the amyloid plaques before the death of the patient, however, had a significant influence on further study of AD and on the development of new active therapy strategies against AD.

At the current time, there is no direct detection of amyloid plaques in the brains of AD patients. The extent of AD is now diagnosed only indirectly based on the brain volume or from metabolic disorders of the brain areas that are affected (MRT and PET). The significant drawback of these methods is, however, only indirect detection of AD, which is often associated with high statistical fluctuation ranges of the results. The detection sensitivity of these methods compared to direct detection of amyloid plaques is therefore considered low.

Several processes for irradiation and imaging diagnoses of biological tissues with long-wave light of the wavelength range of 600 to 1200 nm (near infrared diagnosis) are known. Since biological tissue has a relatively high permeability for long-wave light of this spectral region, another process for graphic tissue visualization is thus available to the diagnostician in addition to modern imaging processes, such as radiography, magnetic resonance tomography or ultrasound diagnosis (Haller, E. B. Time-Resolved Transillumination and Optical Tomography. J Biomed Optics 1996, 1:7–17). The use of NIR radiation for site-dependent recording of blood flow and degree of oxygenation in the brain of infants by the detection of hemoglobin/deoxyhemoglobin absorption is a process that has been known and used for years (Jöbsis, F. F., Noninvasive Infrared Monitoring of Cerebral and Myocardial Oxygen Sufficiency and Circulatory Parameters. Science 1977, 198: 1264–67; Chance, B.; Leigh, J. S., Miyake, H. et al. Comparison of Time-Resolved and Time-Unresolved Measurements of Deoxyglobin in Brain. Proc Natl Acad Sci USA 1988, 85: 4971–75; Benaron, D. A. et al. Optical Time-of-Flight and Absorbance Imaging of Biological Media. Science 1993, 33: 369A).

In near-infrared diagnosis, both the detection of non-absorbed radiation in the form of a transmission visualization and the fluorescence radiation that is emitted after irradiation with near-infrared light can provide tissue-specific data.

The basic problem in the use of near-infrared radiation is the strong scattering of light, so that even in the case of different photophysical properties, this object is poorly distinguished from an object with sharp edges and its surrounding area. The problem grows with increasing removal of the object from the surface and can be seen as a primary limiting factor both in transillumination and in the detection of fluorescence radiation.

The object of the invention is therefore to make available new compounds that overcome the drawbacks of the prior art.

This object is achieved according to the invention in that compounds of general formula I

$$Fm(-A_l)(-B_n)(-W_o) \qquad (I)$$

in which
 F is a dye-signal molecule, which has at least one absorption maximum in the range of 600 to 1200 nm,
 A is a biomolecule that binds to β-amyloid-plaques,
 B is a dye that binds to β-amyloid-plaques,
 W is a hydrophilic, low-molecular structural element that binds to β-amyloid-plaques,
 m stands for number 1 or 2, provided that n and o mean 0, or m stands for an integer 3–20,
 l and n, independently of one another, stand for number 0, 1 or 2,
 o stands for an integer 0, 1, 2, 3 or 4,
 provided that the sum of l, n and o≧1, as well as their physiologically compatible salts, are made available.

It has been found, surprisingly enough, that the compounds according to the invention are stored in or bind to the amyloid plaques or components of the amyloid plaques or are built up there and thus result in a unification and an increase in absorption and fluorescence of the latter in the detecting areas.

The in-vivo detection of β-amyloid deposits with use of NIR radiation requires dyes as contrast media, which have a high absorption and fluorescence quantum yield in the wavelength range of 600 to 1200 nm and bind selectively to β-amyloid deposits.

Dyes from the class of polymethines have absorption and fluorescence properties that are characterized by high molar absorption coefficients between 600 and 1200 nm and adequate fluorescence quantum yields. Dyes of this class generally have high photostability.

It has been found, surprisingly enough, that to improve the differentiation between normal and diseased tissue, fluorescence dyes that accumulate in the diseased tissue or selectively bind to pathologically altered tissue components and have a specific absorption and emission behavior are suitable.

In this invention, it has been found, surprisingly enough, that the compounds of general formula I according to the invention bind to the β-amyloid plaques. The change of the (scattered) irradiated light that is produced by absorption of the dye and/or the fluorescence that is induced by the stimulator radiation is detected and yields the actual tissue-specific data that make possible an assessment on the degree of the pathogenic change.

According to the invention, those dyes are used as signal molecules F that are covalently linked with structures that bind selectively to β-amyloid plaques or are substituted with such structures.

Compounds of general formula I according to the invention are those in which, for example, a) 1 and n mean zero, m stands for one and o stands for 1–4, or b) n and o mean zero, m stands for 3–20 and 1 stands for 1–2, or c) 1 and o mean zero, m stands for 1–2 and n stands for 1–2, provided that the sum of n and m is less than or equal to 3.

Preferred are compounds of general formula I according to the invention, in which F stands for a cyanine, squarilium, croconium, merocyanine or oxonol dye.

Especially preferred are compounds of general formula I, in which F stands for a cyanine, squarilium or croconium dye of general formulas II–IV

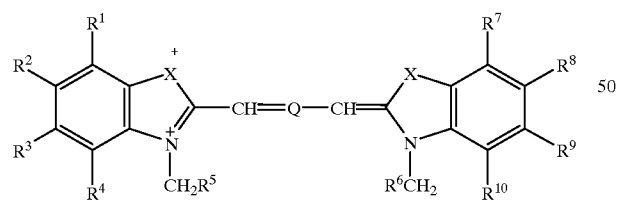
(II)

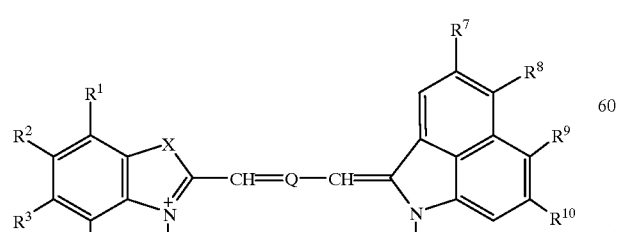
(III)

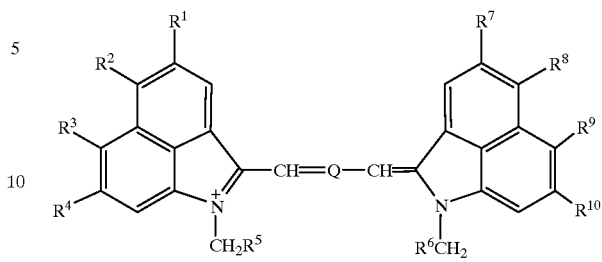
(IV)

in which
R$^1$ to R$^4$ and R$^7$ to R$^{10}$, independently of one another, stand for a fluorine, chlorine, bromine or iodine atom, or a nitro group or for a radical —COOE$^1$, —CONE$^1$E$^2$, —NHCOE$^1$, —NHCONHE$^1$, —NE$^1$E$^2$, —OE$^1$, —OSO$_3$E$^1$, —SO$_3$E$^1$, —SO$_2$NHE$^1$, —E$^1$,
whereby E$^1$ and E$^2$, independently of one another, stand for a hydrogen atom, a saturated or unsaturated, branched or straight-chain C$_1$–C$_{50}$ alkyl chain, whereby the chain or portions of this chain optionally can form one or more aromatic or saturated cyclic C$_5$–C$_6$ units or bicyclic C$_{10}$ units, and whereby the C$_1$–C$_{50}$ alkyl chain is interrupted by 0 to 15 oxygen atoms and/or by 0 to 3 carbonyl groups and/or is substituted with 0 to 5 hydroxy groups,
and whereby in each case adjacent radicals R$_1$–R$_4$ and/or R$_7$–R$_{10}$ can be linked together with the formation of a six-membered aromatic carbon ring, or these radicals stand for a binding to A, B or W,
R$^5$ and R$^6$, independently of one another, stand for a radical —E$^1$ with the above-indicated meaning or for a C$_1$–C$_4$ sulfoalkyl chain,
Q represents a fragment

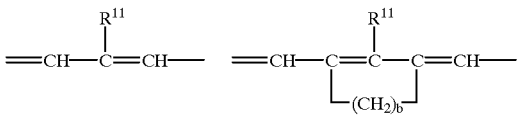

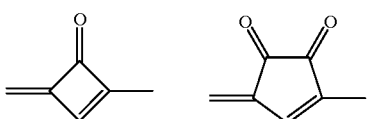

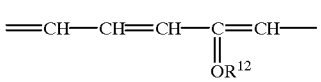

in which
R$^{11}$ stands for a hydrogen, fluorine, chlorine, bromine or iodine atom or a nitro group or a radical —NE$^1$E$^2$, —OE$^1$ or —E$^1$, whereby E$^1$ and E$^2$ have the above-indicated meaning,
R$^{12}$ stands for a hydrogen atom or a radical E$^1$ with the above-indicated meaning, b means a number 0, 2 or 3, X and Y, independently of one another, mean O, S, —CH=CH— or a fragment

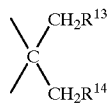

in which
R$^{13}$ and R$^{14}$, independently of one another, stand for hydrogen, a saturated or unsaturated, branched or straight-chain C$_1$–C$_{10}$ alkyl chain, which can be interrupted by up to 5 oxygen atoms and/or substituted with up to 5 hydroxy groups, and whereby radicals R$^{13}$ and R$^{14}$ can be linked together while forming a 5- or 6-membered ring.

Especially preferred are compounds of general formula I, in which F represents a cyanine dye of general formula V

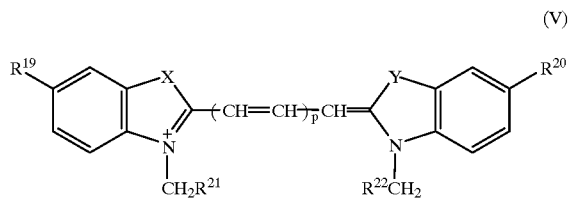

in which
p means an integer 2 or 3,
X and Y, independently of one another, stand for O, S, —CH=CH— or C(CH$_3$)$_2$,
R$^{19}$ and R$^{20}$, independently of one another, represent a radical —COOE$^1$, —CONE$^1$E$^2$, —NHCOE$^1$, —NHCONHE$^1$, —NE$^1$E$^2$, —OE$^1$, —OSO$_3$H, —SO$_3$H, —E$^1$, whereby E$^1$ and E$^2$ have the above-indicated meaning, provided that E$^1$ and E$^2$ are not hydrogen atoms at the same time,
R$^{21}$ and R$^{22}$, independently of one another, stand for a radical —E$^1$ with the above-indicated meaning, for a C$_1$–C$_4$ sulfoalkyl chain
or R$^{19}$, R$^{20}$, R$^{21}$, R$^{22}$, E$^1$ or E$^2$ stands for a binding to A, B or W with the above-indicated meaning.

Especially preferred are also compounds of general formula I, in which F represents a cyanine dye of general formula VI

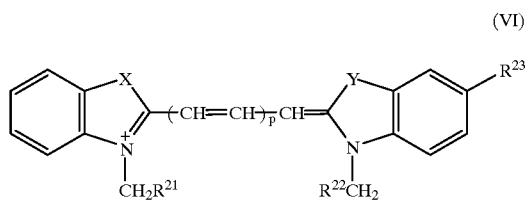

in which
p, X, Y, R$^{21}$ and R$^{22}$ have the above-indicated meaning,
R$^{23}$ stands for —OE$^3$, —COOE$^3$, —CONHE$^3$, —CONH(CH$_2$)$_{1-6}$—NHE$^3$, —CONH(CH$_2$)$_{1-6}$—OE$^3$, —CONH(CH$_2$)$_{1-6}$—COOE$^3$ or —CONH(CH$_2$)$_{1-6}$—CONHe$^3$,
in which
E$^3$ stands for a mono-, oligo- or polysaccharide with at least one radical —OSO$_3$H.

Especially preferred in addition are compounds of general formula I, in which F represents an oxonol dye of general formula VII

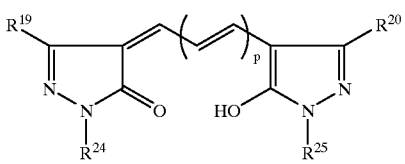

in which
p, R$^{19}$ and R$^{20}$ have the above-indicated meaning,
R$^{24}$ and R$^{25}$, independently of one another, stand for a phenyl ring that is substituted in one to three places with hydroxy, carboxy, sulfate, sulfonate, alkyl or alkoxy or carboxylic acid ester radicals.

Compounds of general formula I according to the invention are those in which A stands for, for example, antibodies, antibody fragments, specific peptide and proteins, receptors, enzymes, enzyme substrates, nucleotides, ribonucleic acids, deoxyribonucleic acids, lipoproteins, carbohydrates; mono-, di- or trisaccharides; linear or branched oligo- or polysaccharides or -saccharide derivatives or for a dextran.

Preferred peptide are the β-amyloid 1–40, 1–42 and 1–43, as well as partial structures and derivatives thereof. Especially preferred are β-amyloids and partial structures of β-amyloids, which are modified with the amino acid cysteine, whereby the binding to F via the sulfhydryl group of the cysteine is carried out by means of a maleimido structure.

Monomeric amino sugars are, for example, glucosamine, galactosamine, mannosamine, gulosamine, fucosamine, 3-amino-3-deoxy-ribose, kanosamine, mycosamine, mycaminose, desosamine, rhodosamine, 6-amino-6-deoxy-glucose, neosamine, paromose.

Amino-sugar carboxylic acids are, for example, glucosaminic acid, glucosaminuronic acid, muramic acid, trehalosamine, chondrosin and derivatives, chitotriose.

Preferred are compounds of general formula I, in which the binding to F between the amino group of the sugar and the carboxy group of the dye is carried out with the formation of an amide group.

In addition, compounds of general formula I with mono-, di-, tri- and oligosaccharides for A, whose glycosidic hydroxy group was converted into an amino group, are preferred, whereby the coupling to a carboxy group of dye F is carried out with the formation of an amide group.

Monomeric to oligomeric saccharides are aldo- and ketotrioses to aldo- and ketoheptoses, ketooctoses and ketononoses, anhydro sugars, cyclites, amino- and diamino sugars, deoxy sugars, aminodeoxy sugars, monocarboxylic acid sugars, amino-sugar-carboxylic acids, aminocyclites, phosphorus-containing derivatives of monomers to oligomers.

Examples of suitable polysaccharides are fucoidan, arabinogalactan, chondroitin and -sulfates, dermatan, heparin, heparan, heparitin, hyaloronic acid, keratan, polygalacturonic acid, polyglucuronic acid, polymannuronic acid, inulin, polylactose, polylactosamine, polyinosinic acid, polysucrose, amylose amylopectin, glycogen, nigeran, pullulan, asparagosin, sinistrin, sitosin, galactocaolose, luteose, galactan, mannans, guaran, glucomannans, galactoglucomannans, phosphomannans, fucans, pectins, cyclodextrins and the chemically and/or enzymatically produced derivatives, decomposition and cleavage products of high-molecular compounds.

Especially preferred mono-, oligo- and polysaccharides are sulfated or polysulfated structures.

Sulfated structures are, for example, glucosamine-3-sulfate, glucosamine-6-sulfate and those structures that can be obtained by sulfation with suitable reagents from the above-described mono-, di-, tri- to oligosaccharides, as well as polysaccharides.

Sulfations, for example according to Jaurand, G., et al., Carbohydrate Research 1994, 255: 295–301; Böcker, T., et al., Carbohydrate Research, 1992, 230: 245–256.

Dye structures B that bind selectively to β-amyloid plaques according to the invention are diazo dyes, which are bonded covalently to the signal molecules. Suitable diazo dyes are, for example, Congo Red, Chrysamine G, Evans Blue, Chicago Sky Blue 6B, Direct Red® dyes, Direct Yellow® dyes, Ponceau® dyes, Reactive Black 5, and Calcion.

Preferred compounds of general formula I are those in which B represents a disazo dye of general formula VIII (VIII)

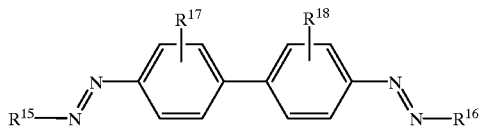

in which $R^{15}$ and $R^{16}$, independently of one another, stand for a phenyl or naphthyl radical that is substituted with one or more hydroxy, carboxy, amino, sulfonic acid, alkoxycarbonyl, alkylamino, dialkylamino, alkoxy groups, with up to 6 carbon atoms in the alkyl radical, or arylsulfonyl groups, with up to 9 carbon atoms in the aryl radical, or $R^{15}$ and $R^{16}$ stand for a dye F, $R^{17}$ and $R^{18}$, independently of one another, stand for a hydroxy, carboxy, sulfonic acid, alkyl, alkoxy radical with up to 6 carbon atoms.

Preferred compounds of general formula I according to the invention are also those in which W stands for a radical —$OSO_3H$ or —$SO_3H$, an unbranched, branched, cyclic or polycyclic alkyl, alkenyl, polyalkenyl, alkinyl, aryl, alkylaryl or arylalkyl radical with up to 60 C atoms, which is substituted with up to 5 hydroxy groups, up to 3 carboxylic acid groups and at least one radical —$OSO_3H$ or —$SO_3H$.

Preferred are those compounds according to general formula I, in which W means a sulfated structure, which can be represented by sulfation of corresponding hydroxy compounds.

Suitable are, for example, amino alcohols, whereby the linkage is carried out between amino group and carboxy group of the dye with the formation of an amide group, and the hydroxy groups are sulfated. Examples of amino alcohols are 2-amino-1-ethanol, 3-amino-1-propanol, 4-amino-1-butanol, 5-amino-1-pentanol, 6-amino-1-hexanol, 3-amino-1,2-propanediol, 2-amino-1,3-propanediol, 3-amino-1,2,4-butanetriol, hdyroxyanilines, 4-aminoresorcinol.

Signal molecules and specifically binding structural units are connected together via commonly used functional groups. Such groups are, for example, esters, ethers, sec ondary and tertiary amines, amides and structures that are cited below

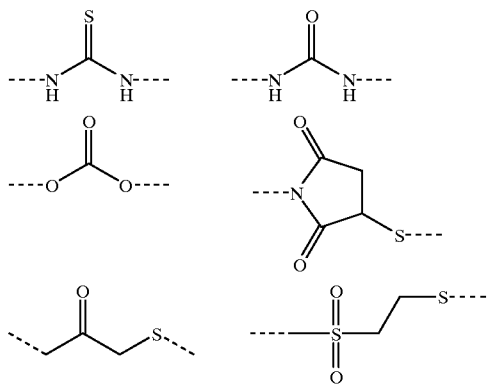

The production of the compounds of general formula I according to the invention is carried out by modification of polymethine-dye-parent substances, which contain fucntionalities that can be coupled (e.g., carboxyl, amino, and hydroxyl groups), according to the processes that are known to one skilled in the art.

Correspondingly, while obtaining the structure of the starting compounds, these groups are modified in a way that is known in the art by reaction with corresponding substituents.

The synthesis of the polymethine-dye-parent substances is carried out according to methods that are known in the literature, for example, F. M. Hamer in *The cyanine Dyes and Related Compounds,* John Wiley and Sons, New York, 1964; *Cytometry,* 10, (1989), 3–10; 11 (1990) 418–430; 12(1990) 723–30; *Bioconjugate Chem.* 4 (1993) 105–11, *Anal. Biochem.* 217 (1994) 197–204, Tetrahedron 45 (1989) 4845–66, EP-0 591 820 A1, *J. Org. Chem.* 60 (1995) 2361–95.

The production of the dye-biomolecule adducts according to the invention (1 does not equate to zero in general formula I) is carried out by reaction of the dye with a biomolecule A according to methods that are known in the literature. The dyes must have reactive groups that can be coupled in this regard or the dye must be activated in-situ or in advance by generation of these groups. With regard to amino- and sulfhydryl groups of a biomolecule, reactive groups are, for example, N-hydroxysuccinimidylester, N-hydroxysuccinimidylester-3-sulfate, isothiocyanates, isocyanates, maleimide-, haloacetyl, vinylsulfone groups. The coupling is preferably carried out in an aqueous medium. In this case, the degree of concentration can be controlled by stoichiometry and reaction time. Literature: *Synth. Commun.* 23 (1993) 3078–94, DE-OS 3912046, *Cancer Immunol. Immunother.* 41 (1995) 257–263, *Cancer Research* 54 (1994) 2643–49.

Another subject of this invention is the use of compounds of general formula I according to the invention for in-vivo diagnosis of neurodegenerative diseases by means of NIR radiation.

Another subject of this invention is the use of compounds of general formula I according to the invention for in-vitro diagnosis.

To this end, tissue samples or biopsy samples are obtained and their contents of β-amyloid-pleated-sheet structures are studied.

Surprisingly enough, the dyes according to the invention bind selectively to the samples that are to be studied and allow an evaluation based on the specifically emitted fluorescence in the near-infrared spectral region.

Another subject of this invention are also diagnostic agents for in-vivo diagnosis, which contain compounds of general formula I together with the commonly used adjuvants and vehicles as well as diluents.

According to the invention, one or more of the substances are fed preferably intrathecally, intralumbarly or intravenously to the tissue in the case of use for in-vivo diagnosis, and light from the near-infrared spectral region is irradiated. The non-absorbed, scattered light and/or scattered fluorescence radiation that is emitted by the dye are recorded simultaneously/individually. Preferred are the methods in which the tissue irradiates over a large surface, and the fluorescence radiation that is resolved locally is visualized by imaging with a CCD camera or the tissue areas that are to be imaged are rastered with a fiber optic light guide, and the signals that are received are converted numerically into a synthetic image. Fluorescence can also be evaluated spectrally and/or by phase selection, as well as in a steady-state manner and/or in a time-resolved manner.

The special advantage of the compounds according to the invention, for example compared to radiodiagnostic processes, lies in the fact that with use of a more stable dye, the fluorescence signal can also be produced and detected after prolonged periods after administration by excitation of the dye. An extended time window for the diagnosis is available, since limitations, for example, by decomposition half-lives do not exist.

With the use according to the invention, a non-invasive diagnostic method is made available, which makes possible the direct detection of the amyloid plaques in vivo.

The examples below explain the invention.

EXAMPLE 1

Production of N-(2,3-disulfato)propyl-1,1'-bis-(4-sulfobutyl)indotricarbocyanine-5-carboxylic acid amide, trisodium salt 1) 1,1'-Bis-(4-sulfobutyl)indotricarbocyanine-5-carboxylic acid-N-hydroxysuccinimidylester, sodium salt 0.15 g (0.75 mmol) of N,N'-dicyclohexylcarbodiimide in 5 ml is added in drops to a solution of 0.5 g (0.7 mmol) of 1,1'-bis-(4-sulfobutyl)indotricarbocyanine-5-carboxylic acid and 0.1 g (0.9 mmol) of N-hydroxysuccinimide in 30 ml of anhydrous DMF at 0° C. under argon. It is stirred for 72 hours at room temperature. Then, the solvent is evaporated in a high vacuum at 40° C. up to about 5 ml, and the residue is stirred with 200 ml of diethyl ether. After the ether is decanted from deposited precipitate, it is mixed again with 5 ml of dimethylformamide, and the described process is repeated. The precipitate that is obtained is dried in a high vacuum and stored under argon at −20° C.

Yield: 0.55 g (97%) of dark blue powder

2) N-(2,3-Dihydroxy)propyl-1,1'-bis-(4-sulfobutyl)-indotricarbocyanine-5-carboxylic acid amide, sodium salt 0.5 g (0.61 mmol) of 1,1'-bis-(4-sulfobutyl)-indotricarbocyanine-5-carboxylic acid-N-hydroxysuccinimidylester in 20 ml of dimethylformamide is mixed with a solution of 0.15 g (0.92 mmol) of 2-aminomethyl-5,5-dimethyl-1,3-dioxolan-hydrochloride and 0.1 g (1.1 mmol) of triethylamine in 20 ml of dimethylformamide, and it is stirred for 24 hours at room temperature. The working-up is carried out as described above. The crude product is stirred in 30 ml of water/MeOH/acetic acid (3:1:2) for 18 hours at room temperature, and the solution is subjected directly to chromatographic purification (Europrep, 60-30 C18, 60A, 20–45 μ, mobile solvent: water/methanol).

Yield: 0.25 g (52%) of blue lyophilizate

3) N-(2,3-Disulfato)propyl-1,1'-bis-(4-sulfobutyl)-indotricarbocyanine-5-carboxylic acid amide, trisodium salt 0.25 g (0.32 mmol) of N-(2,3-dihydroxy)propyl-1,1'-bis-(4-sulfo-butyl)indotricarbocyanine-5-carboxylic acid amide is stirred together with 0.22 g (1.6 mmol) of sulfur trioxide-trimethylamine complex in 15 ml of dimethylformamide for 48 hours at room temperature. The reaction mixture is concentrated by evaporation, stirred with ether, and the precipitated solid is chromatographically purified (Europrep, 60-30 C18, 60A, 20–45μ, mobile solvent: 0.5% NaCl solution/methanol).

Yield: 0.20 g (64%) of blue lyophilizate

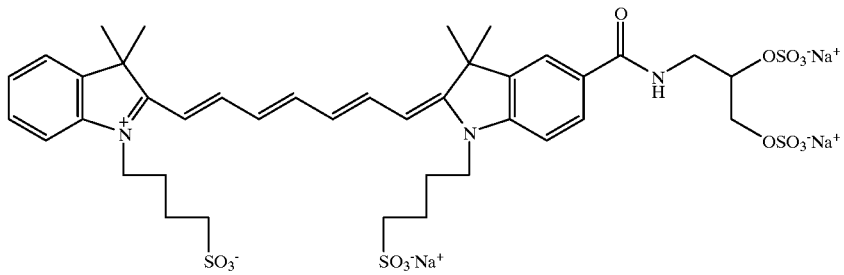

$\lambda_{Max.absorption}(H_2O) = 746$ nm $\lambda_{Max.fluorescenece}(H_2O) = 780$ nm

EXAMPLE 2

Bis-1,1'-(4-Sulfobutyl)indotricarbocyanine-5-carboxylic acid-α-D-glucosamide-3"-sulfate, disodium salt (2)

0.23 g (0.7 mmol) of benzotriazol-1-yl-N,N,N',N'-tetramethyluronium-tetrafluoroborate (TBTU) is added to a solution of 0.5 g (0.7 mmol) of 1,1'-bis-(4-sulfobutyl) indotricarbocyanine-5-carboxylic acid and 0.1 g (1.0 mmol) of triethylamine in 20 ml of anhydrous dimethylformamide. After 30 minutes of stirring at room temperature, a solution of 0.36 g (1.4 mmol) of α-D-glucosamine-3-sulfate and 0.15 g (1.5 mol) of triethylamine in 25 ml of anhydrous dimethylformamide is added in drops. It is stirred for another 3 hours at room temperature, the solvent is evaporated in a high vacuum at 40° C., and the residue is stirred with diethyl ether. The solid that is formed is filtered off and chromatographically purified on RP-silica gel Europrep, 60-30 C18, 60A, 20–45 μ, step gradient: 100% 0.5% NaCl solution→90% 0.5% NaCl solution/10% methanol→90% water/10% methanol→50% methanol) and then freeze-dried.

Yield: 0.51 g (76%) of blue lyophilizate

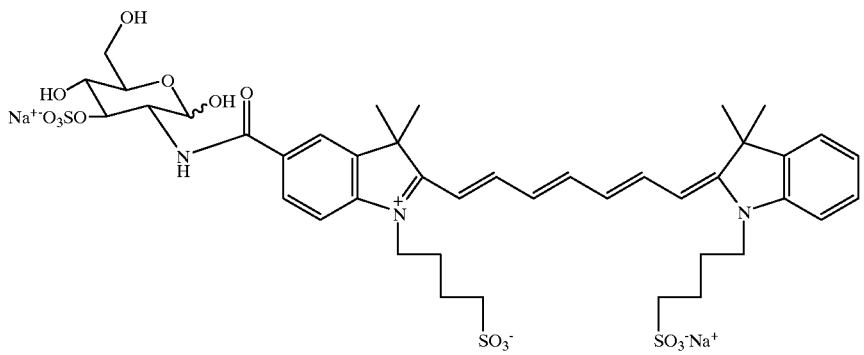

$\lambda_{Max.absorption}(H_2O)$=745 nm $\lambda_{Max.fluorescence}(H_2O)$=779 nm

EXAMPLE 3

Bis-1,1'-(4-Sulfobutyl)indotricarbocyanine-5,5'-dicarboxylic acid-di-α-D-glucosamide-di-3"-sulfate, trisodium salt (3)

The production and purification are carried out analogously to Example 2, starting from 0.5 g (0.66 mmol) of 1,1'-bis-(4-sulfobutyl)indotricarbocyanine-5,5'-dicarboxylic acid, 0.2 g (2.0 mmol) of triethylamine in 25 ml of dimethylformamide, addition of 0.43 g (1.32 mmol) of TBTU as well as 0.69 g (2.64 mmol) of α-D-glucosamine-3-sulfate and 0.3 g (3 mmol) of triethylamine in 30 ml of dimethylformamide.

Yield: 0.56 g (66%) of blue lyophilizate $\lambda_{Max.absorption}(H_2O)$=754 nm $\lambda_{Max.fluorescence}(H_2O)$=790 nm

EXAMPLE 4

N-Chondrosin-bis-1,1'-(4-sulfobutyl)indotricarbocyanine-5-carboxylic acid amide, sodium salt (4)

The production is carried out analogously to Example 2, starting from 0.5 g (0.7 mmol) of 1,1'-bis-(4-sulfobutyl)indotricarbocyanine-5-carboxylic acid with use of 0.43 g (1.2 mmol) of chondrosin. The reaction time is 5 hours. The purification is carried out by means of HPLC (column: 250×20 mm, Nucleosil 100C18, 7 mm, eluant 50 mmol of phosphate buffer pH 4/MeOH, 5% to 95% MeOH in 60 minutes) with subsequent desalination to RP-silica gel and freeze-drying.

Yield: 0.35 g (48%) of blue lyophilizate

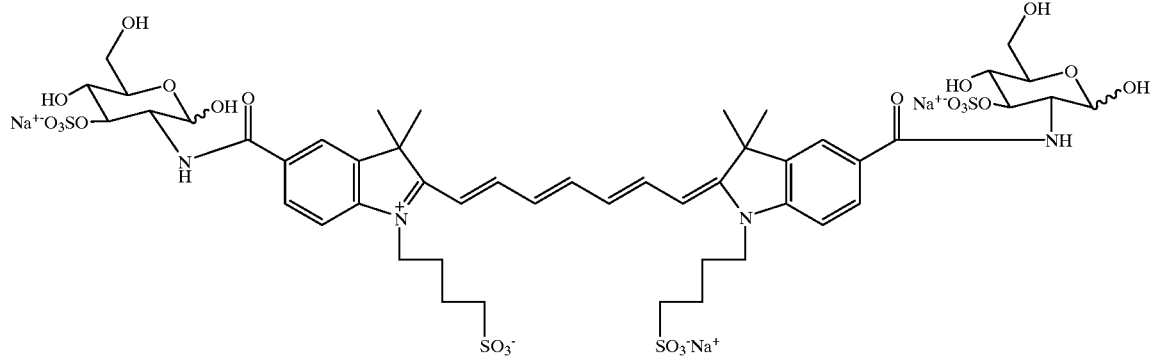

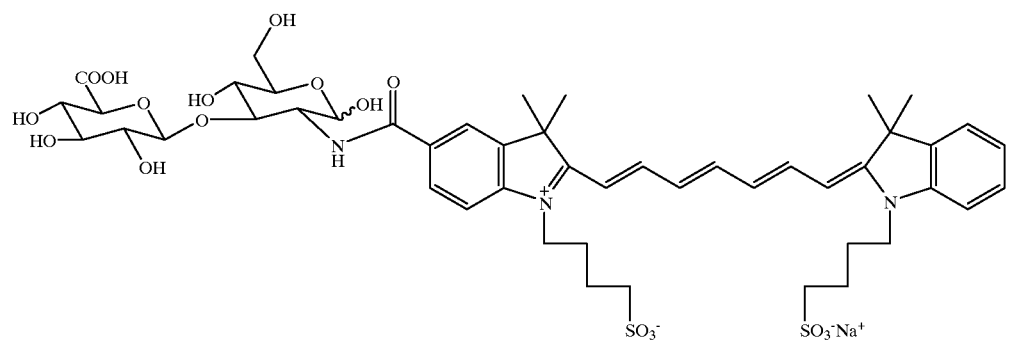

$\lambda_{Max.absorption}(H_2O)$=746 nm $\lambda_{Max.fluorescence}(H_2O)$=779 nm

EXAMPLE 5

Maltotriose-Indotricarbocyanine Adduct

1) Production of 1-amino-1-deoxy-maltotriose 0.2 g of maltotriose is stirred into 5 ml of a saturated ammonium bicarbonate for 7 days at 30° C. To remove excess ammonium bicarbonate, the solution is freeze-dried several times until a constant weight is reached.

2) Coupling with 1,1'-bis-(4-sulfobutyl)indotricarbocyanine-5-carboxylic acid

A solution of 0.1 g (0.14 mmol) of 1,1'-bis-(4-sulfobutyl-indotricarbocyanine-5-carboxylic acid and 15 mg of triethylamine in 5 ml of dimethylformamide is mixed with 0.05 g (0.15 mmol) of O-(benzotriazol-1-yl)-N,N,N',N'-tetramethyl-uronium tetrafluoroborate (TBTU), and it is stirred for 30 minutes at room temperature. Then, 0.14 g (0.28 mmol) of 1-amino-1-deoxy-maltotriose is added and stirred for another 5 hours at room temperature. After the dimethylformamide is removed at 40° C. in a high vacuum, the residue is stirred with ether, filtered off and chromatographically purified (Europrep, 60-30 C18, 60A, 20–45 μ, mobile solvent: water/methanol). Yield after freeze-drying 50%.

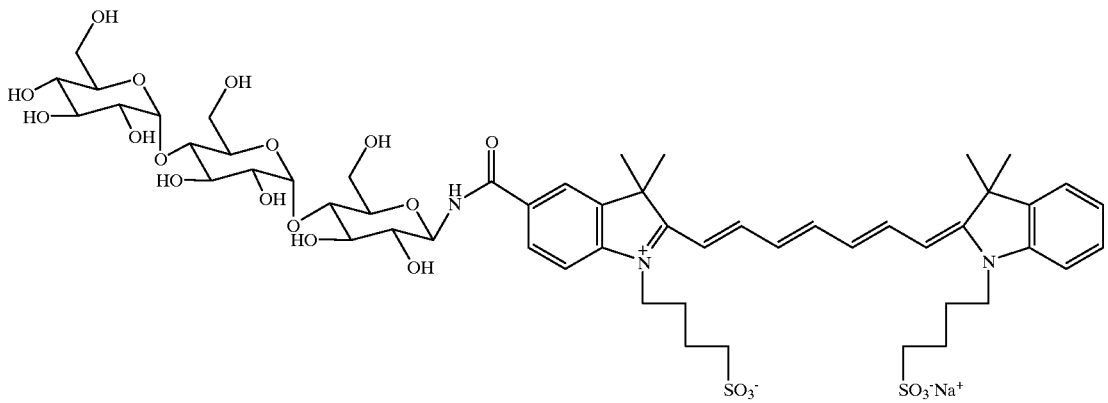

$\lambda_{Max.absorption}(H_2O)$=748 nm $\lambda_{Max.fluorescence}(H_2O)$=779 nm

EXAMPLE 6

Heparin-Indotricarbocyanine Adduct 0.25 g of heparin (low-molecular, M about 6000 g/mol, Sigma Company) is partially de-N-sulfated (25° C. for 3 hours; yield 0.20 g) in a way that is similar to Nagasawa, K. and Inoue, Y. (Methods in Carbohydrate Chemistry Vol. III, 1980, 291–294).

0.10 g of partially de-N-sulfated, low-molecular heparin is mixed in 40 ml of phosphate buffer (0.1 M $NaH_2PO_4$/$Na_2HPO_4$, pH 8.3) with a solution of 0.12 g (0.15 mmol) of 1,1'-bis-(4-sulfobutyl)indotricarbocyanine-5-carboxylic acid-N-hydroxysuccinimidylester, sodium salt (see Example 1) in 4 ml of dimethylformamide, and it is stirred for 2 hours at room temperature. Purification is carried out by means of ultrafiltration with distilled water (Centriprep 3000, Amicon Company), freeze-drying and 5-hour drying at 50° C. in a high vacuum.

| Sulfur content (determination by means of ICP-AES) | |
|---|---|
| S(%) Heparin | 11.55 |
| S(%) partially de-N-sulfated | 10.02 |
| S(%) after labeling with dye | 10.89 |

$\lambda_{Max.absorption}(H_2O)$=750 nm $\lambda_{Max.fluorescence}(H_2O)$=782 nm

EXAMPLE 7

Indotricarbocyanine-cys-β-amyloid Adducts

1) Production of N-[3-(3-maleimidobenzoyl)aminopropyl]-bis-1,1'-(4-sulfobutyl)indotricarbocyanine-5-carboxylic acid amide, sodium salt 1,1'-Bis-(4-sulfobutyl)indotricarbocyanine-5-carboxylic acid is converted into the above-mentioned compound in a way that is similar to processes that are known in the literature by reaction with 3-aminopropyl-t-butylcarbamate, release of the amino group by acidic cleavage with trifluoroacetic acid and reaction with 3-maleimidobenzoic acid chloride.

2a) Labeling of cys-β-amyloid (1–40)

Oxygen is removed from all solvents by saturation with argon.

10 mg of freeze-dried cys-β-amyloid (1–40) is dissolved in 1 ml of phosphate buffer of pH 7.8/DMF (2:1 mixture) and mixed with 10 mg of N-[3-(3-maleimidobenzoyl)aminopropyl]-bis-1,1'-(4-sulfobutyl)indotricarbocyanine-5-carboxylic acid amide, sodium salt. It is stirred for 3 hours at room temperature, diluted with 5 ml of water, and the solution is freeze-dried.

Purification by means of HPLC (column: Merck Select B, 5 μ; mobile solvent: water +0.05% trifluoroacetic acid, acetonitrile) yields 4 mg of product.

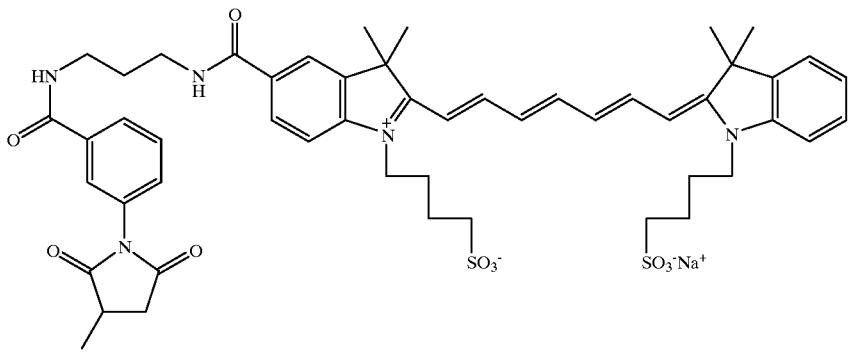

C DAEFR HDSGY EVHHQ KLVFF AEDVG SNKGA IIGLM VGGVV $\lambda_{Max.absorption}(H_2O)=747$ nm $\lambda_{Max.fluorescence}(H_2O)=780$ nm 2b) Labeling of cys-β-amyloid (12–20)

The reaction is carried out analogously to 2a). 5 mg of cys-β-amyloid (12–20) is mixed with 10 mg of dye and stirred for 2.5 hours at room temperature. 6 mg of product is obtained after purification by HPLC.

Before incubation with dyes, the dried membrane was incubated with slight shaking for two hours with TBST-block-buffer (TBST, see above; 5% milk powder) and then washed for 5 minutes with TBST buffer. The incubation with dyes was carried out by slight shaking of membranes in 0.0005–0.05% solutions of the dye in TBST. Then, it was washed five times with TBTS buffer, and the membrane was dried at room temperature and sealed shut.

2) Evaluation by Means of Fluorescence Detection

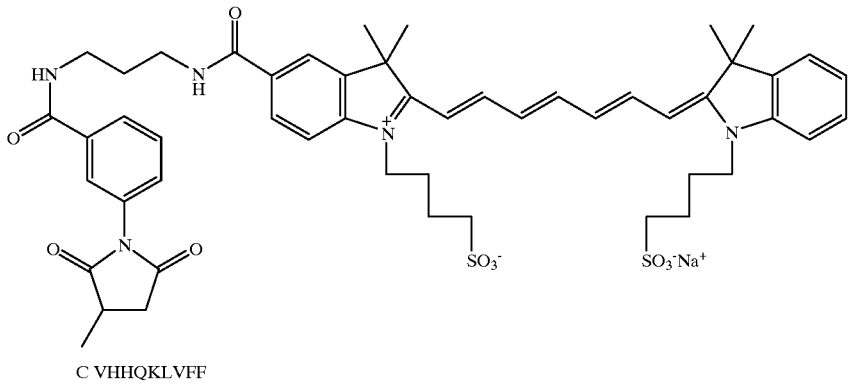

C VHHQKLVFF

EXAMPLE 8

Binding Assay for Measuring the Binding of Dye Constructs to βA4-peptide by Fluorescence Detection 1) Production of βA4-peptide-coated membranes and incubation with βA4-binding dye constructs The binding assay was carried out on βA4-peptide-coated nitrocellulose membranes (cellulose nitrate-membrane filter CN: 0.4 μm, Schleicher & Schuell Company). The coating of the membrane was carried out in a dot-blot-chamber (Stratagene Company). The membrane and the blotting paper (GB002, Schleicher & Schuell Company) was moistened with water and equilibrated in TBST buffer (20 mmol of tris/HCl pH 7.6; 127 mmol of NaCl; 0.1% Tween 20; 0.01% $NaN_3$).

10, 5 and 2.5 μg of peptide in 0.2 ml of TBST buffer were applied to the membrane from a solution of βA4-peptide in water (2 mg/ml). After 15 minutes of incubation, the peptide solution was suctioned through the membrane, flushed with 0.2 ml of TBST buffer, and the membrane was removed from the dot-blot-chamber and dried for 30 minutes at 37° C.

The laser-induced fluorescence pictures are performed on an experimental fluorescence imaging system. The excitation was carried out with monochromatic laser light of wavelength 740 nm by decoupling the radiation via a fiber optic system and homogeneous stimulation of the cellulose membranes. The reflected excitation light is blocked by a cut-off filter, the laser-induced fluorescence light is recorded above 740 nm with a CCD camera (Charge Coupled Device) and the data is stored as black-white images.

Figure 2:
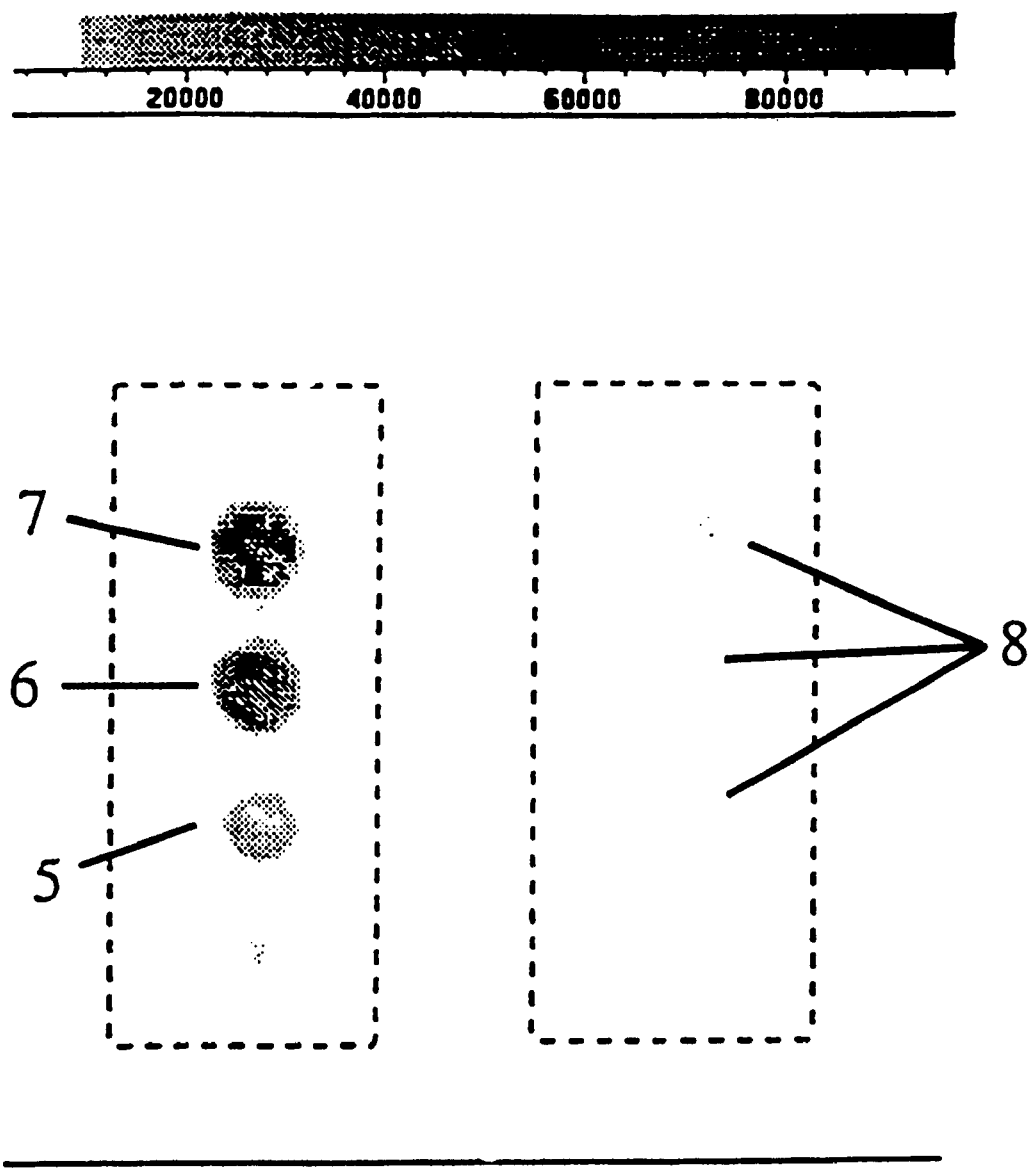

In FIGS. 1 to 2, examples of fluorescence pictures of the membranes are shown.

FIG. 1

Fluorescence picture of the cellulose membrane after incubation with bis-1,1'-(4-sulfobutyl)indotricarbocyanine, sodium salt (0.005% solution).

Excitation wavelength 740 nm, detection>780 nm

1: 2.5 μg of β-amyloid (1–42)
2: 5 μg of β-amyloid (1–42)
3: 10 μg of β-amyloid (1–42)
4: Control peptides with similar binding properties to the cellose membrane

FIG. 2

Fluorescence picture of the cellulose membrane after incubation with 4-[5-[3-carboxy-3-hydroxy-1-(4-sulfophenyl)-1H-pyrazol-4-yl]-2,4-pentadienylidene]-4,5-dihydro-5-oxo-1-(4-sulfobutyl)-1H-pyrazole-3-carboxylic acid, dipotassium salt (0.005% solution)
Excitation wavelength 650 nm, detection>680 nm 5: 2.5 μg of β-amyloid (1–42)
    6: 5 μg of β-amyloid (1–42)
    7: 10 μg of β-amyloid (1–42)
    8: Control peptides with similar binding properties to the cellulose membrane.

What is claimed is:

1. A compound of formula I

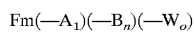

in which

A is a biomolecule that binds to β-amyloid-plaques,

B is a dye that binds to β-amyloid-plaques,

W is a hydrophilic, low-molecular structural element that binds to β-amyloid-plaques, m stands for number 1 or 2, or provided that n and o mean 0, m stands for an integer 3–20, l and n, independently of one another, stand for number 0, 1 or 2, o stands for an integer 0, 1, 2, 3 or 4, provided that the sum of l, n and o $\geq 1$, and F is a dye-signal molecule, which has at least one absorption maximum in the range of 600 to 1200 nm, which is (a) a cyanine dye of formula V

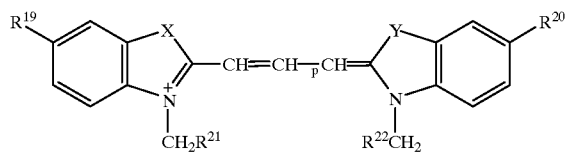

in which p means an integer 2 or 3,

X and Y, independently of one another, stand for O, S, —CH=CH— or C(CH$_3$)$_2$, $R^{19}$ and $R^{20}$, independently of one another, represent a radical —COOE$^1$, —CONE$^1$E$^2$, —NHCOE$^1$, —NHCONHE$^1$, —NE$^1$E$^2$, —OE$^1$, —OSO$_3$H, —SO$_3$H, —E$^1$, wherein E$^1$ and E$^2$, independently of one another, stand for a hydrogen atom, a saturated or unsaturated, branched or straight-chain C$_1$–C$_{50}$ alkyl chain, wherein the chain or portions of this chain optionally forms one or more aromatic or saturated cyclic C$_5$–C$_6$ units or bicyclic C$_{10}$ units, and wherein the C$_1$–C$_{50}$ alkyl chain is interrupted by 0 to 15 oxygen atoms and/or by 0 to 3 carbonyl groups and/or is substituted with 0 to 5 hydroxy groups, provided that E$^1$ and E$^2$ are not hydrogen atoms at the same time, and $R^{20}$ is not a hydrogen atom, and $R^{21}$ and $R^{22}$, independently of one another, stand for a radical —E$^1$ with the above-indicated meaning, for a C$_1$–C$_4$ sulfoalkyl chain or $R^{19}$, $R^{20}$, $R^{21}$, $R^{22}$, E$^1$ or E$^2$ binds to A, B or W, (b) a cyanine dye of formula VI

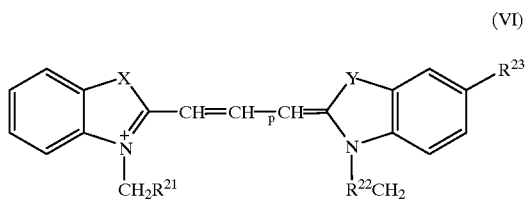

in which p, X, Y, $R^{21}$ and $R^{22}$ have the above-indicated meaning and, $R^{23}$ stands for —OE$^3$, —COOE$^3$, —CONHE$^3$, —CONH (CH$_2$)$_{1-6}$—NHE$^3$, —CONH(CH$_2$)$_{1-6}$—OE$^3$, —CONH (CH$_2$)$_{1-6}$—COOE$^3$ or —CONH(CH$_2$)$_{1-6}$—CONHE$^3$, in which E$^3$ stands for a mono-, oligo- or polysaccharide with at least one radical —OSO$_3$Hx, or (c) an oxonol dye of formula VII

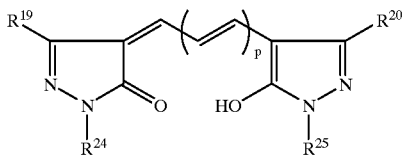

in which p, $R^{19}$ and $R^{20}$ have the above-indicated meaning, and $R^{24}$ and $R^{25}$, independently of one another, stand for a phenyl ring that is substituted in one to three places with a hydroxy, carboxy, sulfate, sulfonate, alkyl or alkoxy or carboxylic acid ester radical, or a physiologically compatible salt thereof.

2. A compound according to claim 1, wherein A stands for an antibody fragment, peptide or protein, receptor, enzyme, enzyme substrate, nucleotide, ribonucleic acid, deoxyribonucleic acid, lipoprotein, carbohydrate, mono-, di or trisaccharide; linear or branched oligo- or polysaccharide or dextran.

3. A compound according to claim 1, wherein
B represents a diazo dye of formula VIII

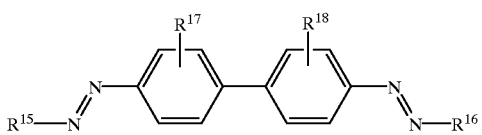

in which $R^{15}$ and $R^{16}$, independently of one another, stand for a phenyl or naphthyl radical that is substituted with one or more hydroxy, carboxy, amino, sulfonic acid, alkoxycarbonyl, alkylamino, dialkylamino, alkoxy groups, with 0 to 6 carbon atoms in the alkyl radical, or an arylsulfonyl group, with 0 to 9 carbon atoms in the aryl radical, or $R^{15}$ and $R^{16}$ stand for a dye F, and $R^{17}$ and $R^{18}$, independently of one another, stand for a hydroxy, carboxy, sulfonic acid, alkyl, alkoxy radical, with 0 to 6 carbon atoms.

4. A compound according to claim 1, wherein

W stands for a radical —$OSO_3H$ or —$SO_3H$, an unbranched, branched, cyclic or polycyclic alkyl, alkenyl, polyalkenyl, alkinyl, aryl, alkylaryl or arylalkyl radical with 0 to 60 C atoms, which is substituted with 0 to 5 hydroxy groups, 0 to 3 carboxylic acid groups and at least one radical —$OSO_3H$ or —$SO_3H$, provided that W is not $(CH_2)_3$—$CH_2SO_3^-$ or $(CH_2)_3$—$CH_2SO_3H$.

5. A compound according to claim 1, wherein F is bound to A, B and/or W, independently of one another, via an ester, ether, secondary or tertiary amino group, amide group or via a group

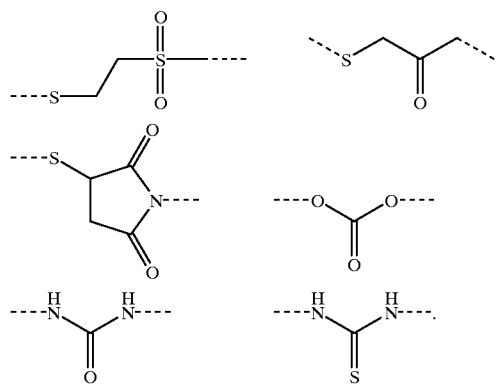

6. A compound according to claim 1, wherein A is β-amyloid 1–40, 1–42 or 1–43.

7. A compound according to claim 1, wherein A is a β-amyloid modified with the amino acid cysteine, whereby the binding to F via the sulfhydryl group of the cysteine is by means of a maleimido structure.

8. A compound according to claim 1, wherein A is glucosamine, galactosamine, mannosamine, gulosamine, fucosamine, 3-amino-3-deoxy-ribose, kanosamine, mycosamine, mycaminose, desosamine, rhodosamine, 6-amino-6-deoxy-glucose, neosamine, or paromose.

9. A compound according to claim 1, wherein A is glucosaminuronic acid, miuramic acid, trehalosamine, chondrosin, or chitotriose.

10. A compound according to claim 1, wherein A is a monomeric to oligomeric saccharide.

11. A compound according to claim 3, wherein A is fucoidan, arabinogalactan, chondroitin or a sulfate thereof, dermatan, heparin, heparan, heparitin, hyaloronic acid, keratan, polygalacturonic acid, polyglucuronic acid, polymannuronic acid, inulin, polylactose, polylactosamine, polyinosinic acid, polysucrose, amylose amylopectin, glycogen, nigeran, pullulan, asparagosin, sinistrin, sitosin, galactocaolose, luteose, galactan, mannans, guaran, glucomannan, galactoglucomannan, phosphomannan, fucans pectin, or cyclodextrin.

12. A compound according to claim 1, wherein F stands for a dye of Formula III

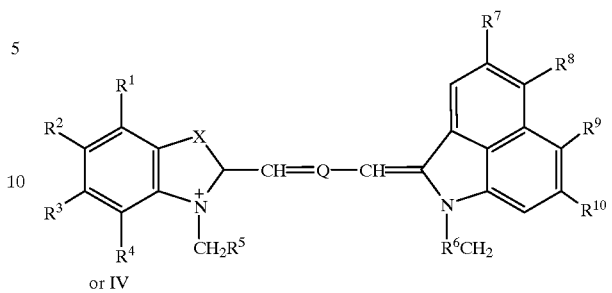

or IV

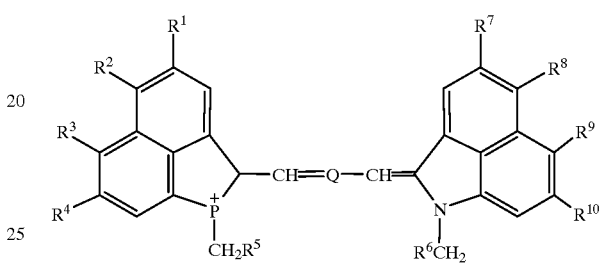

in which $R^1$ to $R^4$ and $R^7$ to $R^{10}$, independently of one another, stand for a fluorine, chlorine, bromine or iodine atom, or a nitro group, or for a radical —$COOE^1$, —$CONE^1E^2$, —$NHCOE^1$, —$NHCONHE^1$, —$NE^1E^2$, —$OE^1$, —$OSO_3E^1$, —$SO_3E^1$, —$SO_2NHE^1$, or —$E^1$, and wherein in each case adjacent radicals $R_1$–$R_4$, or $R_7$–$R_{10}$, or both are linked together to form a six-membered aromatic carbon ring, or these radicals bind to to A, B or W, $R^5$ and $R^6$, independently of one another, stand for a radical —$E^1$ with the above-indicated meaning or for a $C_1$-$C_4$ sulfoalkyl chain, Q represents a fragment

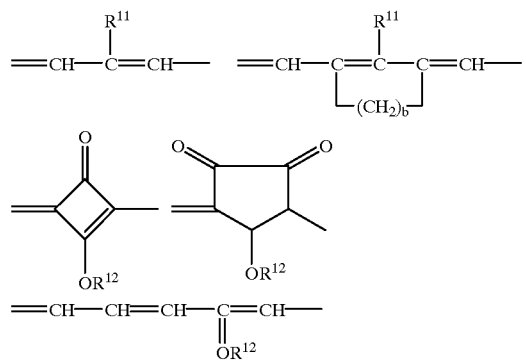

in which $R^{11}$ stands for a hydrogen, fluorine, chlorine, bromine or iodine atom or a nitro group or a radical —$NE^1E^2$, —$OE^1$ or —$E^1$, wherein $E^1$ and $E^2$ have the above-indicated meaning, $R^{12}$ stands for a hydrogen atom or a radical $E^1$ with the above-indicated meaning, b means a number 0, 2 or 3, and X means O, S, —CH=CH— or a fragment

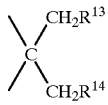

in which

R$^{13}$ and R$^{14}$, independently of one another, stand for hydrogen, a saturated or unsaturated, branched or straight-chain C$_1$–C$_{10}$ alkyl chain, which are interrupted by 0 to 5 oxygen atoms, or substituted with 0 to 5 hydroxy groups, or both, and wherein radicals R$^{13}$ and R$^{14}$ form a 5- or 6-membered ring.

13. The compound of formula I of claim 1, wherein E$^1$ and E$^2$, independently of one another, further stand for a saturated or unsaturated, branched or straight-chain C$_1$–C$_{50}$ alkyl chain, wherein the chain or portions of this chain form one or more aromatic or saturated cyclic C$_5$–C$_6$ moieties or bicyclic C$_{10}$ moieties.

14. The compound of formula I of claim 1, wherein F is a dye-signal molecule which has at least one absorption maximum in the range of 700 to 1200 nm.

15. The compound of formula I of claim 13, wherein F is a dye-signal molecule which has at least one absorption maximum in the range of 700 to 1200 nm.

16. A compound according to claim 1, wherein the monomeric to oligomeric saccharide is an aldo- or ketotriose to aldo- or ketoheptose, ketooctose or ketononose, anhydro sugar, cyclite, amino- or diamino sugar, deoxy sugar, aminodeoxy sugar, monocarboxylic acid sugar, amino-sugar-carboxylic acid, or aminocyclite.

17. A compound according to claim 1, wherein A is a phosphate of a monomeric to oligomeric saccharide.

18. A method of in-vivo diagnosis of neurodegenerative diseases by NIR radiation, comprising using a compound according to claim 1 effective to bind to a pre-existing amyloid plaque.

19. An optical diagnostic agent for in-vivo diagnosis of neurodegenerative diseases by means of NIR radiation, comprising at least one compound according to claim 1 and an adjuvant, vehicle, or diluent or a combination thereof.

20. The method of claim 18, wherein the neurodegenerative disease is Alzheimer's disease.

21. The method of claim 18, wherein the neurodegenerative tissue is from a patient suffering from Alzheimer's disease.

* * * * *

UNITED STATES PATENT AND TRADEMARK OFFICE
CERTIFICATE OF CORRECTION

PATENT NO. : 6,329,531 B1  Page 1 of 1
DATED : December 11, 2001
INVENTOR(S) : Turner et al.

It is certified that error appears in the above-identified patent and that said Letters Patent is hereby corrected as shown below:

Column 17,
Line 40, reads "$-CH=CH-_pCH= =$" should read -- $-(CH=CH)_p-CH=$ --
Lines 57-59, reads "chain, wherein the chain or portions of this chain optionally forms one or more aromatic or saturated cyclic $C_5$-$C_6$ units or bicyclic $C_{10}$ units, and wherein" should read -- chain, wherein --
Line 61, reads "atoms and/or by 0 to 3 carbonyl groups and/or is" should read -- atoms or by 0 to 3 carbonyl groups or is --
Line 62, reads "0 to 5 hydroxy groups, provided that" should read -- 0 to 5 hydroxy groups, or a combination thereof, provided that --

Column 18,
Line 6, reads " $-CH=CH-_pCH= =$ " should read -- $-(CH=CH)_p-CH=$ --

Column 19,
Line 51, reads "miuramic acid" should read -- muramic acid --

Column 20,
Line 24, reads  should read

Line 51, second compound is missing a double bond.

Signed and Sealed this

Twenty-fourth Day of May, 2005

JON W. DUDAS
*Director of the United States Patent and Trademark Office*